(12) United States Patent
Dahlberg et al.

(45) Date of Patent: Mar. 6, 2007
(10) Patent No.: US 7,187,983 B2

(54) ELECTRODE HEAD FIXATION ARRANGEMENT

(75) Inventors: Kenneth Dahlberg, Stockholm (SE); Rolf Hill, Jarfalla (SE)

(73) Assignee: St. Jude Medical AB, Jarfalla (SE)

( * ) Notice: Subject to any disclaimer, the term of this patent is extended or adjusted under 35 U.S.C. 154(b) by 551 days.

(21) Appl. No.: 10/432,064

(22) PCT Filed: Dec. 17, 2001

(86) PCT No.: PCT/SE01/02810

§ 371 (c)(1), (2), (4) Date: May 19, 2003

(87) PCT Pub. No.: WO02/49715

PCT Pub. Date: Jun. 27, 2002

(65) Prior Publication Data

US 2004/0034401 A1 Feb. 19, 2004

(30) Foreign Application Priority Data

Dec. 20, 2000 (SE) .................................. 0004765

(51) Int. Cl.
A61N 1/05 (2006.01)

(52) U.S. Cl. ..................................................... 607/128

(58) Field of Classification Search ................ 607/126, 607/128
See application file for complete search history.

(56) References Cited

U.S. PATENT DOCUMENTS

| 4,409,994 | A | | 10/1983 | Doring |
| 4,913,147 | A | | 4/1990 | Fahlstrom et al. |
| 4,957,118 | A | | 9/1990 | Erlebacher |
| 5,257,634 | A | * | 11/1993 | Kroll ........................... 607/122 |
| 5,957,966 | A | * | 9/1999 | Schroeppel et al. ......... 607/122 |
| 2003/0045919 | A1 | * | 3/2003 | Swoyer et al. .............. 607/122 |

FOREIGN PATENT DOCUMENTS

WO    WO 98/20933    5/1998

* cited by examiner

*Primary Examiner*—George R. Evanisko
*Assistant Examiner*—Michael Kahelin
(74) *Attorney, Agent, or Firm*—Schiff Hardin LLP

(57) ABSTRACT

A fixation arrangement on the outer surface of an electrode head at distal end of a pacing lead includes an attachment mechanism having at least one tine, the tine being connected to the electrode head by a tine base portion that includes an electrically controlled heat-responsive positioner. The electrically controlled heat responsive positioner allows the angular position of the tine relative to the electrode head to be selective adjusted by a temperature change in the positioner.

11 Claims, 2 Drawing Sheets

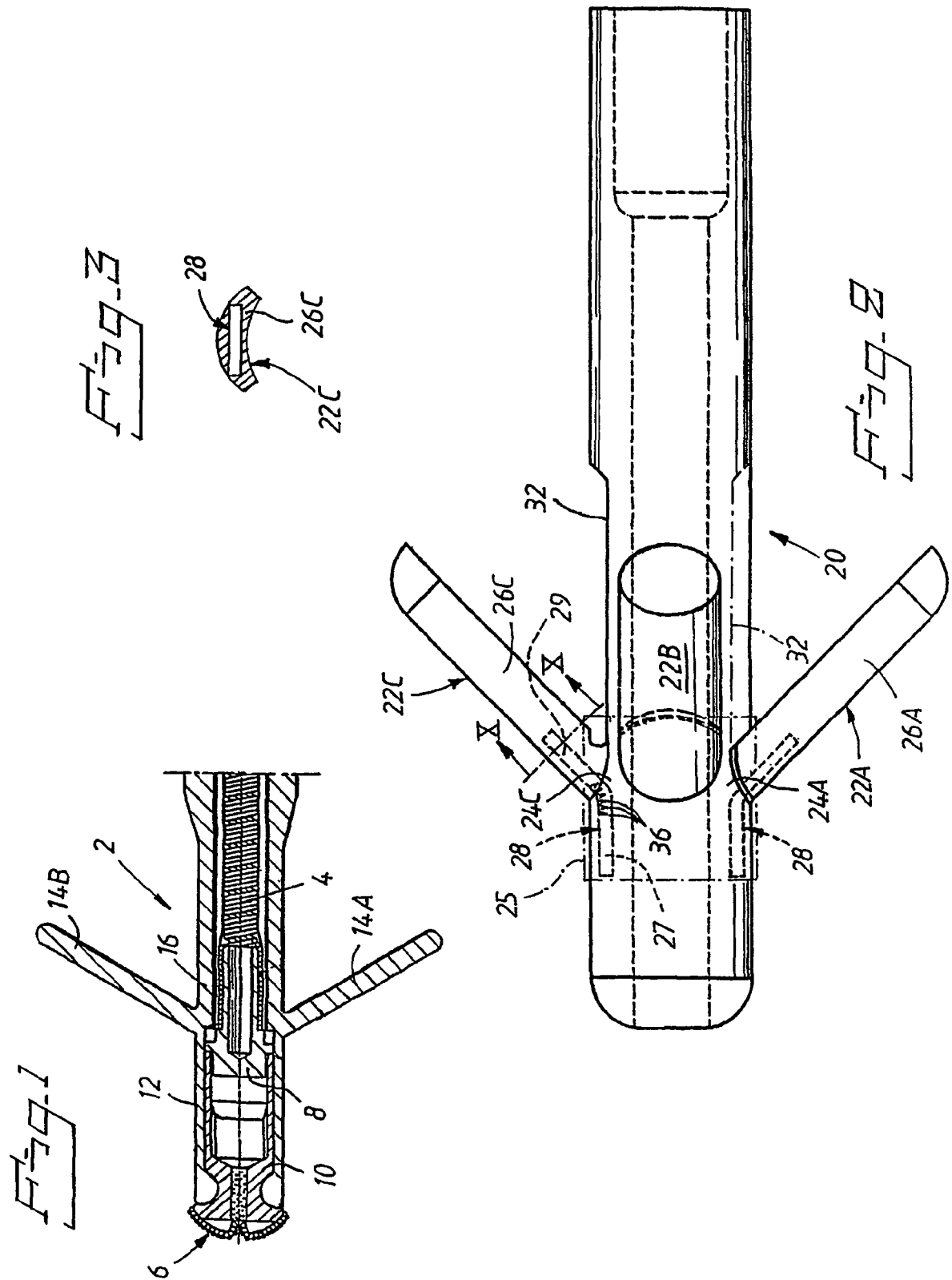

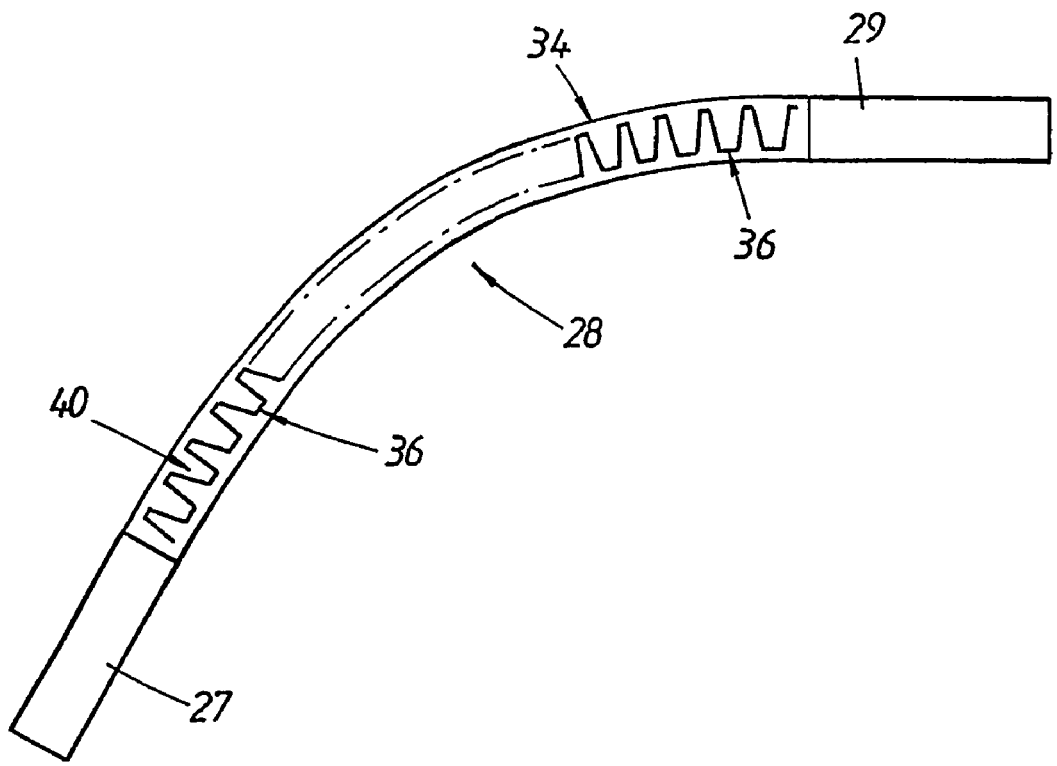
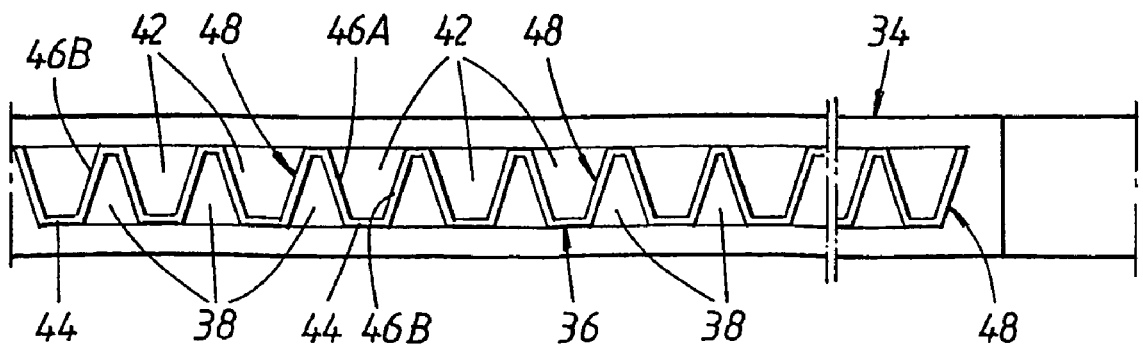

ELECTRODE HEAD FIXATION ARRANGEMENT

BACKGROUND OF THE INVENTION

1. Field of the Invention

The present invention relates to a fixation arrangement on the outer surface of an electrode head mounted at a distal end of a pacing lead.

2. Description of the Prior Art

A pacing lead may be a multipolar (or unipolar or bipolar) electrode lead used for providing intracardial stimulation of heart tissue, and/or for sensing heart signals, by means of a pulse generator or some other type of heart stimulation apparatus. The pacing lead carries the stimulus from the pulse generator to the cardiac tissue, or relays intrinsic cardiac signals back to a sense amplifier of such a pulse generator. The fixation arrangement on the outer surface of the electrode head normally includes an attachment mechanism with one or more tines (and/or fins) adapted to lodge in the trabeculae lining the inner wall of the heart without actually penetrating the cardiac wall.

A tined electrode head (i.e. an electrode head provided with tines) is useful for providing reliable anchoring of the electrode head and its lead in the trabeculae (trabecular network) inside the heart. The barb or fluke-like tines become entangled in the trabecular network thereby securing the electrode head position.

Although tines are very effective for anchoring the electrode head, implantation and repositioning procedures may be facilitated if the tines are foldable and extendable as for instance disclosed in U.S. Pat. No. 4,957,118. This document illustrates a mechanical way of extending and folding the tines by means of a threaded stylet.

SUMMARY OF THE INVENTION

An object of the present invention is to provide an alternative, improved electrode head fixation arrangement having one or more foldable and extendable tines.

Another object of the invention is to provide tine controllability by electric means.

The above object is achieved in accordance with the principles of the present invention in a fixation arrangement on the outer surface of an electrode head disposed at a distal end of a pacing lead, the fixation arrangement including an attachment mechanism including at least one tine, connected to the electrode head by a tine base portion which includes an electrically controlled heat-responsive positioner, allowing adjustment of the angular position of the tine relative to the electrode head dependent on a temperature change in the heat-responsive positioner.

The core of the invention is that each tine is connected to the electrode head by a tine base portion which includes a heat responsive positioner allowing the position of the tine to be adjusted in relation to the electrode head by a temperature change brought about in the heat responsive positioning means.

Since the inventive features the directionality of the individual tine protruding from the outer surface of the electrode head to be changed it is possible to eliminate interference problems which may otherwise—as a result of the configuration of the tines—be encountered during implantation (or repositioning) of the pacing lead and its electrode head. Interference problems with the trabeculae may also be avoided or at least reduced due to the controllability of the "movable tines".

When the electrode head is provided with a number of tines circumferentially spaced apart around the electrode head the tine base portions may constitute integrated parts of the exterior of the electrode head. However, the base portions may instead be integrated parts of a separate tines-carrying element (e.g. in the form of a ring) attached to the exterior of the electrode head. Furthermore, the tines may have their base portions positioned in the same annular region on the electrode head surface. However, it also is possible to use a tines assembly wherein some of the tines have their base portions positioned in a first annular region, and the remaining tines have their base portions placed in a different, second annular region which is axially spaced from the first annular region.

In a preferred embodiment the positioner in each tine base portion has an adjustable hinge element including a sequence of co-operating bending actuators connected in series. Each such bending actuator may be a so-called polyimide micro-joint, in the hinge element the sequence of bending actuators is adapted to allow an adjustable relative angular movement (remote-controlled adjustable bending angle) between a first rigid hinge element part, which is connected to the electrode head, and a second rigid hinge element part, which is anchored to the respective tine in the area of the base portion thereof.

Some basic designs/structures of and operation principles for polyimide micro-joint actuators have been described in various scientific papers and discussed during international workshops. An example is "Three dimensional silicon triple-hot-wire anemometer based on polyimide joints" by Th. Ebefors, E. Kälvesten and G. Stemme, presented at IEEE Int. Workshop on Micro Electro Mechanical System (MEMS '98), Heidelberg, Germany, Jan. 25–29, 1998.

In order to provide a suitable tined electrode head, each tine base portion thereof may be positioned at a forward end of a matching elongated recess in the outer surface of the electrode head. This recess is shaped to extend axially along the electrode head and is dimensioned so that it will accommodate (within a cylindrical outer contour of the electrode head) the tine when it has been folded down to an axial position adjacent to and along the head.

To facilitate a required adjustment of the position of a tine controlled heating of the polyimide material in the bending actuators is included in the hinge element of the tine. Preferably, this is an integrated electric heater. In the sequence of co-operating bending actuators included in the hinge element, each bending actuator preferably has two or more silicon plate sections interconnected by at least one polyimide filled V-groove joint. In an embodiment each bending actuator has at least three silicon plate sections interconnected by two polyimide filled V-groove joints.

Preferably, the integrated electric heater is a resistor in each V-groove. Suitably, layers of electrically conductive material, e.g. aluminum, constitute each such resistor. These electrically conductive material layers are preferably linings on the V-groove surfaces of each V-groove joint.

Preferably, each tine has a non-adjusted initial position wherein the elongated tine body protruding from the tine base portion makes an acute angle, e.g. 45°, with the longitudinal axis of the electrode head.

DESCRIPTION OF THE DRAWINGS

FIG. 1 shows, in a longitudinal section, the forward portion of a conventional electrode head including an attachment mechanism with non-adjustable tines.

FIG. 2 is a schematic side view of an electrode head having on its outer surface a fixation arrangement according to the invention.

FIG. 3 shows a cross section (at line X—X in FIG. 2) of one of the tines on the electrode head in FIG. 2.

FIG. 4 is (on a larger scale) a schematic longitudinal section of the micro-joint hinge element indicated (by broken line) in the base portion of one of the tines on the electrode head in FIG. 2.

FIG. 5 is (on a still larger scale) a longitudinal section, schematically and on a distorted scale, the basic construction of the micro-joint hinge element in FIG. 4.

DESCRIPTION OF THE PREFERRED EMBODIMENTS

FIG. 1 shows the forward portion of an electrode head 2 mounted at a distal end of a bipolar pacing lead of which only the outer coil conductor 4 is visible. The conductor 4 is connected to the tip electrode 6 via connecting means 8, 10. The electrode head 2 is provided with a fixation arrangement on its outer surface 12. In this case the fixation arrangement has at least two, but preferably four or six, tines 14A, 14B etc. These tines, which are formed as protruding integrated parts of the wall 16 of the electrode head 2, constitute non-adjustable tines extending (in their free unloaded state) in a backward direction and making a fixed, non-adjustable angle with the outer surface 12.

In contrast to the electrode head 2 in FIG. 1, the electrode head 20 shown in FIG. 2 is provided on its outer surface with a fixation arrangement including an attachment mechanism having four adjustable tines 22A, 22B, 22C and (not visible) being spaced apart around the circumference of the electrode head 20. The adjustability of the tines means that the angular position of each tine in relation to the electrode head 20 can be controlled and adjusted at the discretion of an operator who is performing an implantation or repositioning (in a human heart) of a pacing lead at the distal end of which the electrode head 20 is mounted. Each tine 22A, 22B, etc. is connected to the electrode head by a transition portion constituting an integrated tine base portion, such as base portions 24A and 24C referenced for tines 22A and 22C, respectively, as examples. Each integrated tine base portion, such as base portions 24A and 24C, includes a heat responsive positioner allowing the tine position to be adjusted by bringing about a temperature change in the heat responsive positioner. In an alternative embodiment the aforementioned base portions constitute integral parts of a ring-shaped tines carrier 25 attached to the exterior of the electrode head 20.

In the tine configuration shown in FIG. 2 all the tines have their respective base portions (such as a base portion 24A) positioned within one and the same annular region on the outer surface of the electrode head 20. Furthermore, all the tines have elongated tine bodies (such as tine bodies 26A and 26C referenced as examples, for tines 22A and 22C, respectively) protruding from their respective base portions (such as portions 24A and 24C) with the same angle of inclination to the longitudinal axis of the electrode head 20.

The adjustability of each tine is provided by the respective heat responsive positioner thereof forming an integral part of the tine and being substantially included in the transitional base portion of the tine. This heat responsive positioner has an angularly adjustable hinge element 28 including a plurality of co-operating bending actuators 36 connected in series. Each bending actuator is a so-called polyimide micro-joint, which will be further elucidated below with reference to FIGS. 4 and 5.

As shown in FIG. 2, for simplicity only in connection with the tine 22C, the tine base portion 24C is positioned at a forward end of an elongated recess 32 in the outer surface of the electrode head 20. This recess extends axially along the electrode head and is dimensioned so that it will accommodate (within a cylindrical envelope of the head) the tine body 26C when same has been angularly retracted (i.e. folded down) to a deactivated "parking position" adjacent to the bottom surface of the recess 32. In FIG. 3 there is shown a suitable cross section of the tine body 26C, at line X—X in FIG. 2. Although not shown in FIG. 2, the other three tines 22A, 22B and the further tine that is not visible would in practice also have their own recesses corresponding to recess 32.

A suitable type and structure of the adjustable (bendable) hinge element 28 included in the base portion of each tine will now be described more in detail, with reference to FIGS. 4 and 5.

The adjustable hinge element 28 has a bendable insulating casing 34 made of a suitable polymer. In the casing 34 there are included a sequence of co-operating bending actuators 36 connected in series to be able to provide, together, a reversible, total 180° adjusting (bending) angle to make possible to turn the tine from a fully retracted backward position (in recess 32) to a fully forward position, which will to a great extent facilitate a pacing lead explantation. The hinge element 28 may have a first inflexible or non-bending part 27 connected to the electrode head 20, and a second non-bending part 29 anchored to the tine base portion 24 or the tine body 26.

Each bending actuator 36 has two silicon plate sections or beam sections 38 interconnected by an intermediate polyimide filled V-groove joint 40. The polyimide filling in each joint 40 is formed by a cured polyimide body 42 positioned in a support channel (defining the V-groove) having a bottom portion 44 and a pair of opposite flanks 46A and 46B, these being integral parts of a cross corrugated metal foil strip 48. The V-groove angle between the flanks 46A, 46B forms a dynamic and reversible "bending angle" or "adjusting angle". The magnitude of this bending/adjusting angle can be changed by electrically controlling the thermal expansion of the cured polyimide body 42. In this case the metal foil strip 48 is used as a resistive heater producing local heat dissipation (temperature increase) in the polyimide body of the joint 40. A temperature increase in the polyimide body 42 results in an expansion of the polyimide, thereby providing a dynamic change of the bending angle. A large total bending angle, e.g. 180°, can be obtained by connecting in series a plurality of V-groove joints 40. Each actuator 36 (V-groove micro-joint 40) will be able to provide say 40 maximum adjustability, so that a series of about 45–50 cooperating actuators (micro-joints) will be required for obtaining a total bending angle of 180°.

Instead of using a metal foil strip 48 as a heater for controlling the expansion of the heat responsive polyimide bodies 42, it is also possible to use some other type of heater, e.g. an electric heating arrangement fully integrated (embedded or contained) in the polyimide bodies 42. Regardless of the type of heater used for controlling the bending angles of the V-groove micro-joints 40 it is only required to have such a heater connected to a pair of electric wires (pole means) for supplying the electric current necessary to provide the required local heat dissipation in the joints.

If the pacing lead (being provided with the electrode head 20 at its distal end) is a bipolar electrode lead it would be suitable to use the two (coil) conductors thereof as the poles for supplying the current needed for the heating of the heat responsive positioner in the hinge element 28.

Although modifications and changes may be suggested by those skilled in the art, it is the invention of the inventors to embody within the patent warranted heron all changes and modifications as reasonably and properly come within the scope of their contribution to the art.

The invention claimed is:

1. A fixation arrangement comprising:
   a pacing lead electrode head having an outer surface;
   at least one line having a tine base portion connecting said tine to said electrode head;
   said tine base portion including an electrically controlled heat-responsive positioner allowing selective angular positioning of said tine relative to said electrode head dependent on a temperature change in said heat-responsive positioner, and
   said positioner in said tine base portion comprising a first rigid hinge element connected to said pacing lead electrode head and a second rigid hinge element anchored to said tine at said tine base portion, and an adjustable hinge element including a sequence of cooperating bending actuators connected in series, each of said bending actuators being a polyimide micro-joint, said sequence producing an adjustable relative angular movement between said first said hinge element and said second rigid hinge element.

2. A fixation arrangement as claimed in claim 1 comprising at least two tines spaced apart around a circumference of said electrode head and each having a tine base portion integrated into said outer surface of said electrode head.

3. A fixation arrangement as claimed in claim 2 wherein each tine base portion is disposed within a same angular region around said outer surface of said electrode head.

4. A fixation arrangement as claimed in claim 2 wherein said tines include a first group of tines and a second group of tines, the respective base portions of said tines in said first group being disposed in a first annular region around said outer surface of said electrode head, and the respective base portions of said tines in said second group being disposed in a second annular region around said outer surface of said electrode head, said first and second annular regions being axially spaced from each other.

5. A fixation arrangement as claimed in claim 1 comprising at least two tines and further comprising a carrier disposed around said outer surface of said electrode head, a respective tine based portions of said tines being integrated in said carrier.

6. A fixation arrangement as claimed in claim 5 wherein each tine base portion is disposed within a same angular region around said outer surface of said carrier.

7. A fixation arrangement as claimed in claim 5 wherein said tines include a first group of tines and a second group of tines, the respective base portions of said tines in said first group being disposed in a first annular region around said outer surface of said carrier, and the respective base portions of said tines in said second group being disposed in a second annular region around said outer surface of said carrier, said first and second annular regions being axially spaced from each other.

8. A fixation arrangement as claimed in claim 1 comprising a heater disposed in at least one of said first rigid hinge element and said second rigid hinge element for controllably heating said polyimide micro-joint.

9. A fixation arrangement as claimed in claim 1 wherein said outer surface of said electrode head has, for each of said tines, a recess disposed axially along said electrode head adjacent said tine base portion to receive said tine when said tine has an angular position of 0° relative to said electrode head.

10. A fixation arrangement as claimed in claim 1 wherein said tine is disposed at a non-adjusted initial position relative to said electrode head wherein said tine forms an acute angle in a range between 30° and 60° relative to a longitudinal axis of said electrode head.

11. A fixation arrangement as claimed in claim 1 wherein said heat-responsive positioner consists of heat-responsive material, and wherein a remainder of said at least one tine consists of material different from said heat-responsive material.

* * * * *